(12) United States Patent
Hyde et al.

(10) Patent No.: US 8,788,380 B2
(45) Date of Patent: Jul. 22, 2014

(54) PROGRAMMED DISPENSING OF CONSUMABLE COMPOSITIONS

(75) Inventors: Roderick A. Hyde, Redmond, WA (US);
Eric D. Leuthardt, St. Louis, MO (US);
Robert W. Lord, Seattle, WA (US);
Clarence T. Tegreene, Bellevue, WA
(US); Lovell L. Wood, Jr., Bellevue, WA
(US)

(73) Assignee: The Invention Science Fund I, LLC, Bellevue, WA (US)

( * ) Notice: Subject to any disclaimer, the term of this patent is extended or adjusted under 35 U.S.C. 154(b) by 1330 days.

(21) Appl. No.: 11/998,461

(22) Filed: Nov. 29, 2007

(65) Prior Publication Data

US 2009/0144189 A1    Jun. 4, 2009

(51) Int. Cl.
*G06Q 40/00* (2012.01)

(52) U.S. Cl.
USPC .............................................. 705/35; 705/38

(58) Field of Classification Search
USPC ........................................................ 705/35
See application file for complete search history.

(56) References Cited

U.S. PATENT DOCUMENTS

| | | | |
|---|---|---|---|
| 4,223,801 A | 9/1980 | Carlson | |
| 4,310,103 A | 1/1982 | Reilly, Jr. et al. | |
| 4,641,692 A | 2/1987 | Bennett | |
| 4,823,982 A | 4/1989 | Aten et al. | |
| 4,899,839 A | 2/1990 | Dessertine et al. | |
| 5,221,024 A | 6/1993 | Campbell | |
| RE34,337 E | 8/1993 | Bennett | |
| 5,329,459 A | 7/1994 | Kaufman et al. | |
| 5,342,518 A | 8/1994 | Posner et al. | |
| 5,372,276 A | 12/1994 | Daneshvar | |
| 5,408,443 A * | 4/1995 | Weinberger | 368/10 |
| 5,454,406 A | 10/1995 | Rejret et al. | |
| 5,522,525 A | 6/1996 | McLaughlin et al. | |
| 5,651,887 A | 7/1997 | Posner et al. | |
| 5,681,507 A | 10/1997 | Kazuma | |
| 5,752,621 A | 5/1998 | Passamante | |
| 5,826,217 A * | 10/1998 | Lerner | 702/177 |
| 5,850,344 A | 12/1998 | Conkright | |
| 5,851,445 A | 12/1998 | Kazuma | |
| 5,955,009 A | 9/1999 | Kazuma | |
| 5,958,307 A | 9/1999 | Kazuma | |
| 5,971,594 A | 10/1999 | Sahai et al. | |
| 6,054,928 A | 4/2000 | Lemelson et al. | |
| 6,068,156 A | 5/2000 | Liff et al. | |
| 6,113,080 A | 9/2000 | Kazuma | |
| 6,182,453 B1 | 2/2001 | Forsberg | |
| 6,183,691 B1 | 2/2001 | Swank et al. | |
| 6,249,717 B1 | 6/2001 | Nicholson et al. | |
| 6,252,494 B1 | 6/2001 | Howell | |
| 6,263,259 B1 | 7/2001 | Bartur | |

(Continued)

OTHER PUBLICATIONS

U.S. Appl. No. 12/927,038, Hyde et al.

*Primary Examiner* — Kirsten Apple
(74) *Attorney, Agent, or Firm* — Suiter Swantz pc llo (57) ABSTRACT

Methods and systems for administering consumable compositions according to a programmed dosing schedule are provided.
A method for administering a consumable composition may comprise one or more of the following steps: (a) dispensing a dose of a consumable composition according to a programmed dosing schedule; and (b) detecting an aspect of the consumable composition.
A system for administering a consumable composition may comprise: (a) means for dispensing a dose of a consumable composition according to a programmed dosing schedule; and (b) means for detecting an aspect of the consumable composition.

22 Claims, 10 Drawing Sheets

(56) References Cited

U.S. PATENT DOCUMENTS

| | | |
|---|---|---|
| 6,304,797 B1 | 10/2001 | Shusterman |
| 6,330,957 B1 | 12/2001 | Bell-Greenstreet |
| 6,332,100 B1 | 12/2001 | Sahai et al. |
| 6,490,920 B1 | 12/2002 | Netzer |
| 6,529,801 B1 | 3/2003 | Rosenblum |
| 6,539,281 B2 | 3/2003 | Wan et al. |
| 6,604,650 B2 | 8/2003 | Sagar |
| 6,625,518 B2 | 9/2003 | Depeursinge |
| 6,636,780 B1 | 10/2003 | Haitin et al. |
| 6,684,920 B2 | 2/2004 | Seitz et al. |
| 6,697,704 B2 | 2/2004 | Rosenblum |
| 6,732,884 B2 | 5/2004 | Topliffe et al. |
| 6,766,218 B2 | 7/2004 | Rosenblum |
| 6,773,668 B1 * | 8/2004 | Everson et al. .................. 422/28 |
| 6,801,123 B2 | 10/2004 | Brakus |
| 6,856,932 B1 | 2/2005 | Wallace |
| 6,892,941 B2 | 5/2005 | Rosenblum |
| 7,072,738 B2 | 7/2006 | Bonney et al. |
| 7,175,081 B2 | 2/2007 | Andreasson et al. |
| 7,295,890 B2 | 11/2007 | Jean-Pierre |
| 7,440,818 B2 | 10/2008 | Handfield et al. |
| 7,444,203 B2 | 10/2008 | Rosenblum |
| 7,454,267 B2 | 11/2008 | Bonney et al. |
| 7,469,820 B2 | 12/2008 | Rosenblum |
| 7,471,993 B2 | 12/2008 | Rosenblum |
| 7,502,664 B2 | 3/2009 | Berg |
| 7,516,082 B2 | 4/2009 | Sanville et al. |
| 7,630,791 B2 | 12/2009 | Nguyen et al. |
| 7,715,277 B2 | 5/2010 | de la Huerga |
| 7,774,097 B2 | 8/2010 | Rosenblum |
| 7,804,419 B2 | 9/2010 | Hyde et al. |
| 7,831,336 B2 | 11/2010 | Gumpert |
| 7,844,361 B2 | 11/2010 | Jean-Pierre |
| 7,907,477 B2 | 3/2011 | Puzia |
| 8,019,471 B2 | 9/2011 | Bogash et al. |
| 8,060,249 B2 | 11/2011 | Bear et al. |
| 8,068,015 B2 | 11/2011 | Burg |
| 8,116,907 B2 | 2/2012 | Hyde et al. |
| 8,195,330 B2 | 6/2012 | Coe |
| 8,325,011 B2 | 12/2012 | Butler et al. |
| 8,362,914 B2 | 1/2013 | Hyde et al. |
| 8,457,783 B2 | 6/2013 | Hyde et al. |
| 2001/0011501 A1 | 8/2001 | Sato et al. |
| 2001/0045242 A1 | 11/2001 | Clusserath et al. |
| 2002/0001535 A1 | 1/2002 | Weng |
| 2002/0088817 A1 | 7/2002 | Bell-Greenstreet |
| 2003/0050731 A1 | 3/2003 | Rosenblum |
| 2003/0084957 A1 | 5/2003 | Seitz et al. |
| 2003/0088332 A1 | 5/2003 | Rosenblum |
| 2003/0093181 A1 | 5/2003 | Rosenblum |
| 2003/0220608 A1 | 11/2003 | Huitt et al. |
| 2004/0163970 A1 | 8/2004 | Sin et al. |
| 2004/0164146 A1 | 8/2004 | Rosenblum |
| 2004/0215369 A1 | 10/2004 | Rosenblum |
| 2004/0249250 A1 | 12/2004 | McGee et al. |
| 2005/0065645 A1 | 3/2005 | Liff et al. |
| 2006/0097000 A1 | 5/2006 | Gumpert |
| 2006/0259195 A1 | 11/2006 | Eliuk et al. |
| 2006/0266763 A1 | 11/2006 | Svabo Bech |
| 2006/0283876 A1 | 12/2006 | Mocnik et al. |
| 2007/0145067 A1 | 6/2007 | Headlee |
| 2007/0184219 A1 * | 8/2007 | Johnson ..................... 428/34.1 |
| 2007/0293982 A1 | 12/2007 | Rosenblum |
| 2008/0173705 A1 | 7/2008 | Girard et al. |
| 2008/0195251 A1 | 8/2008 | Milner |
| 2008/0283542 A1 | 11/2008 | Lanka et al. |
| 2009/0048712 A1 | 2/2009 | Rosenblum |
| 2009/0057341 A1 * | 3/2009 | Girard et al. ............... 222/129.1 |
| 2009/0134181 A1 | 5/2009 | Wachman et al. |
| 2010/0324728 A1 | 12/2010 | Rosenblum |

\* cited by examiner

PROGRAMMED DISPENSING OF CONSUMABLE COMPOSITIONS

BACKGROUND

Programmed regimens of consumable compositions may be prescribed by a physician or may simply be desirable for the health and well-being of an individual. However, confusion may arise concerning the schedule, dosage, and/or compliance with a programmed dosing regimen.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Figure 1:
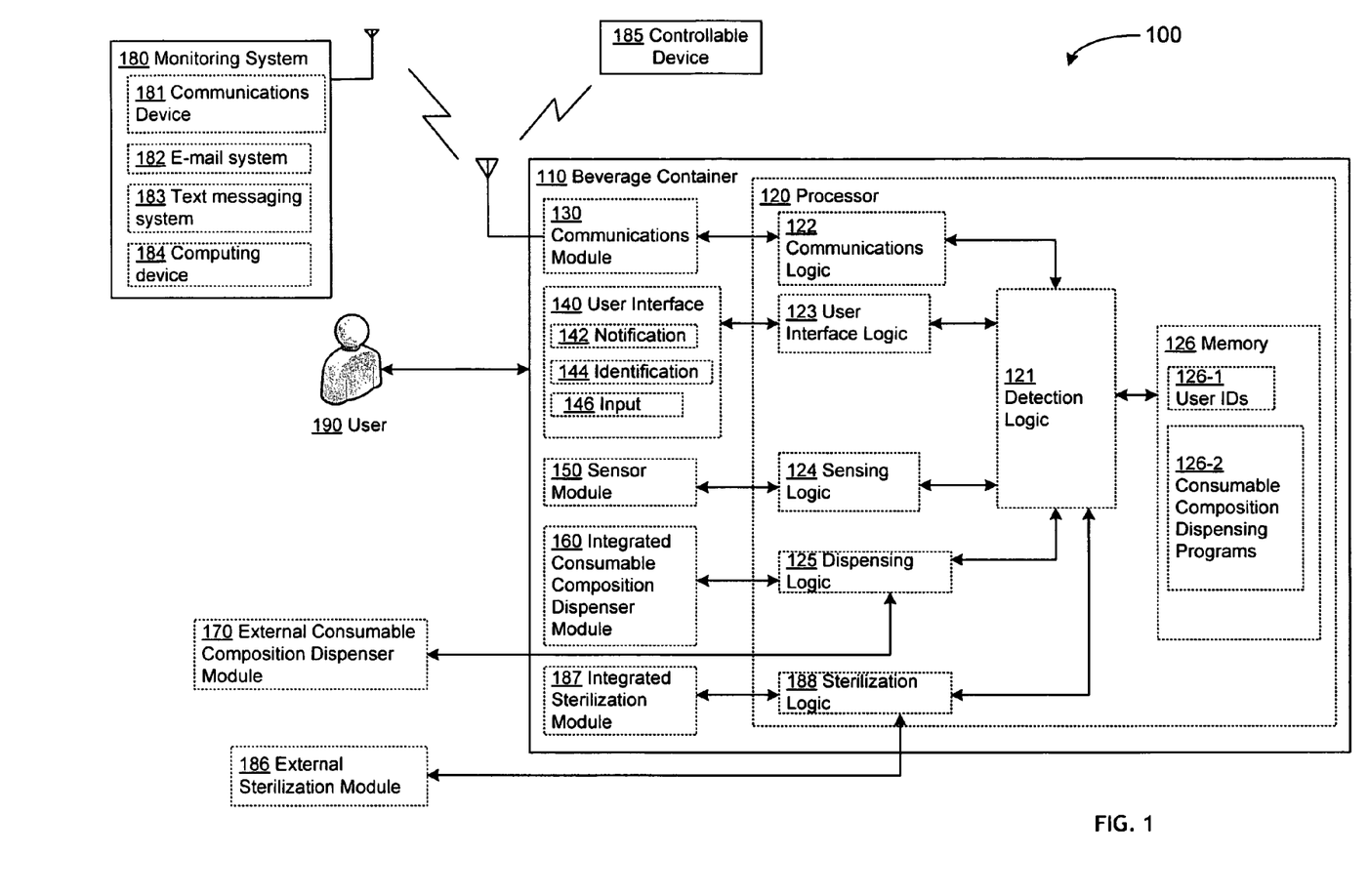
FIG. 1 shows a high-level block diagram of a beverage container.

FIG. 1 illustrates an example environment in which one or more technologies may be implemented. A consumable composition dispensing system 100 may comprise a beverage container 110 to be used by user 190. The beverage container 110 may include a processor 120, a communications module 130, a user interface 140, a sensor module 150, an integrated consumable composition dispenser module 160, and/or an integrated sterilization module 187.

Processor 120 may include detection logic 121, communications logic 122, user interface logic 123, sensing logic 124, dispensing logic 125, memory 126, and/or sterilization logic 188.

Memory 126 may include user identification data 126-1 and/or consumable composition dispensing programs 126-2.

User interface 140 may include a notification module 142, an identification module 144, and/or a user input module 146.

Sensor module 150 may include one or more of a light source sensor, a position sensor, an emission sensor, a spectrophotometer, an infrared or ultraviolet sensor, a biometric sensor, and the like.

The consumable composition dispensing system 100 may further include an external consumable composition dispenser 170 and/or external sterilization module 186.

Figure 2:
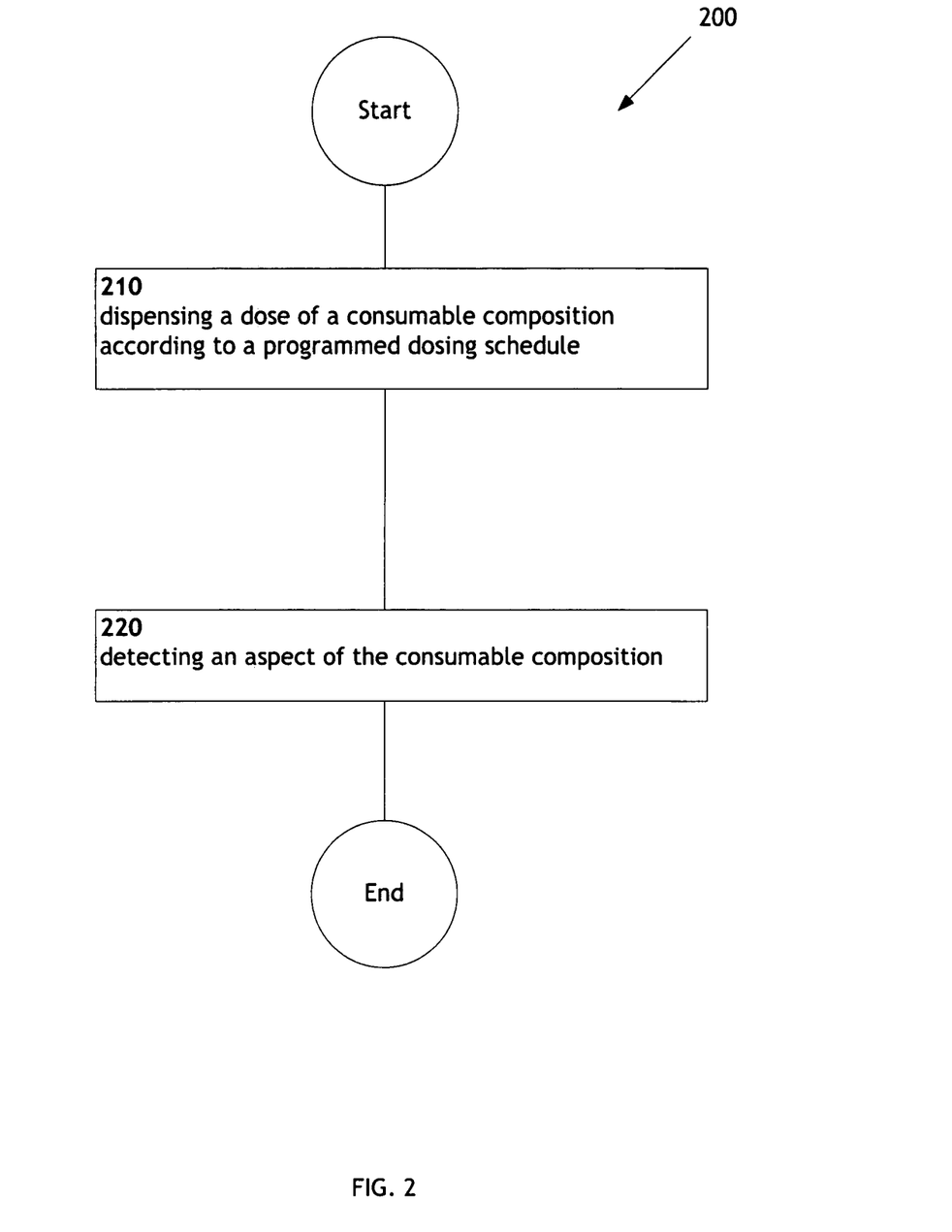
FIG. 2 is a high-level logic flowchart of a process.

FIG. 2 illustrates an operational flow 200 representing example operations related to programmed dispensing of consumable compositions. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to a dispensing operation 210, where a dose of a consumable composition may be dispensed according to a programmed dosing schedule. For example, as shown in FIG. 1, an integrated consumable composition dispenser module 160, and/or an external consumable composition dispenser module 170 may distribute one or more doses (e.g. 30 mg) of a consumable composition (e.g., an anti-depressant, such as Paroxotene) into a beverage container 110 (e.g., a drinking cup) according to a programmed dosing schedule (e.g. electronic data representing a physician-prescribed regimine of medication maintained in memory 126).

Then, in a detecting operation 220, an aspect of the consumable composition may be detected. For example, as shown in FIG. 1, an aspect (e.g. an amount dispensed) of the consumable composition may be detected by detection logic 121 receiving data from sensing logic 124 operably coupled to a sensor module 150 (e.g. a capacitive concentration sensor), communications logic 122 operably coupled to a communications module 130 (e.g. a wireless transceiver), user interface logic 123 operably coupled to a user interface 140 (e.g. a keypad or touchscreen), dispensing logic 125 operably coupled to an integrated consumable composition dispenser module 160, and/or an external consumable composition dispenser module 170 (e.g. an actuated relase mechanism), and/or sterilization logic 188 operably coupled to a sterilization module 186, 187 (e.g. an ultra-violet radiation source).

The aspect of the consumable composition may include, but is not limited to, an amount of consumable composition dispensed into the beverage container 110, an amount of consumable composition present in the beverage container 110, an amount of the composition removed from the beverage container 110, an identity (e.g. a chemical composition) of the consumable composition, an identity of a user 190 (e.g. a fingerprint), a user input 146, a programmed schedule for dispensing the consumable composition, and the like.

The aspect of the consumable composition may be communicated via the communication module 130 to an outside entity. The outside entity may be a monitoring system 180 (e.g. a LAN associated with a physician's office) or a controllable device 185 which may be controlled according to the aspect of the consumable composition (e.g. a cell phone).

Figure 3:
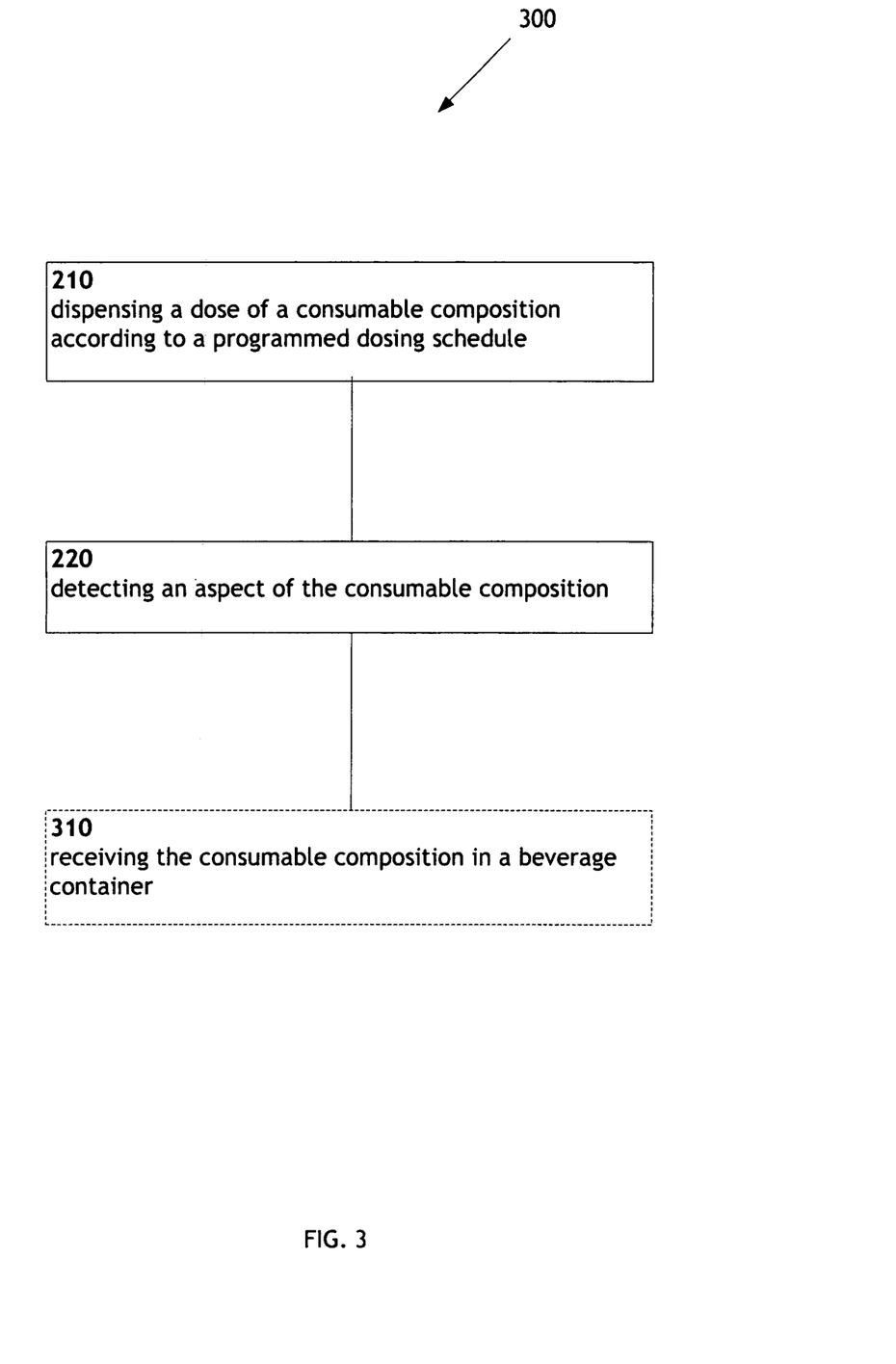
FIG. 3 is a high-level logic flowchart of a process.

FIG. 3 illustrates an operational flow 300 representing example operations related to programmed dispensing of consumable compositions. FIG. 3 illustrates an example embodiment where the example operational flow 200 of FIG. 2 may include at least one additional operation. Additional operations may include an operation 310.

After a start operation, a dispensing operation 210, and a detecting operation 220, the operational flow 300 moves to a receiving operation 310, where a consumable composition may be received in a beverage container 110. For example, as shown in FIG. 1, the beverage container 110 may include any receptacle configured for retaining liquid or gel composition. The beverage container may include a cup, glass, mug, bowl, pitcher, jug, and the like.

Figure 4:
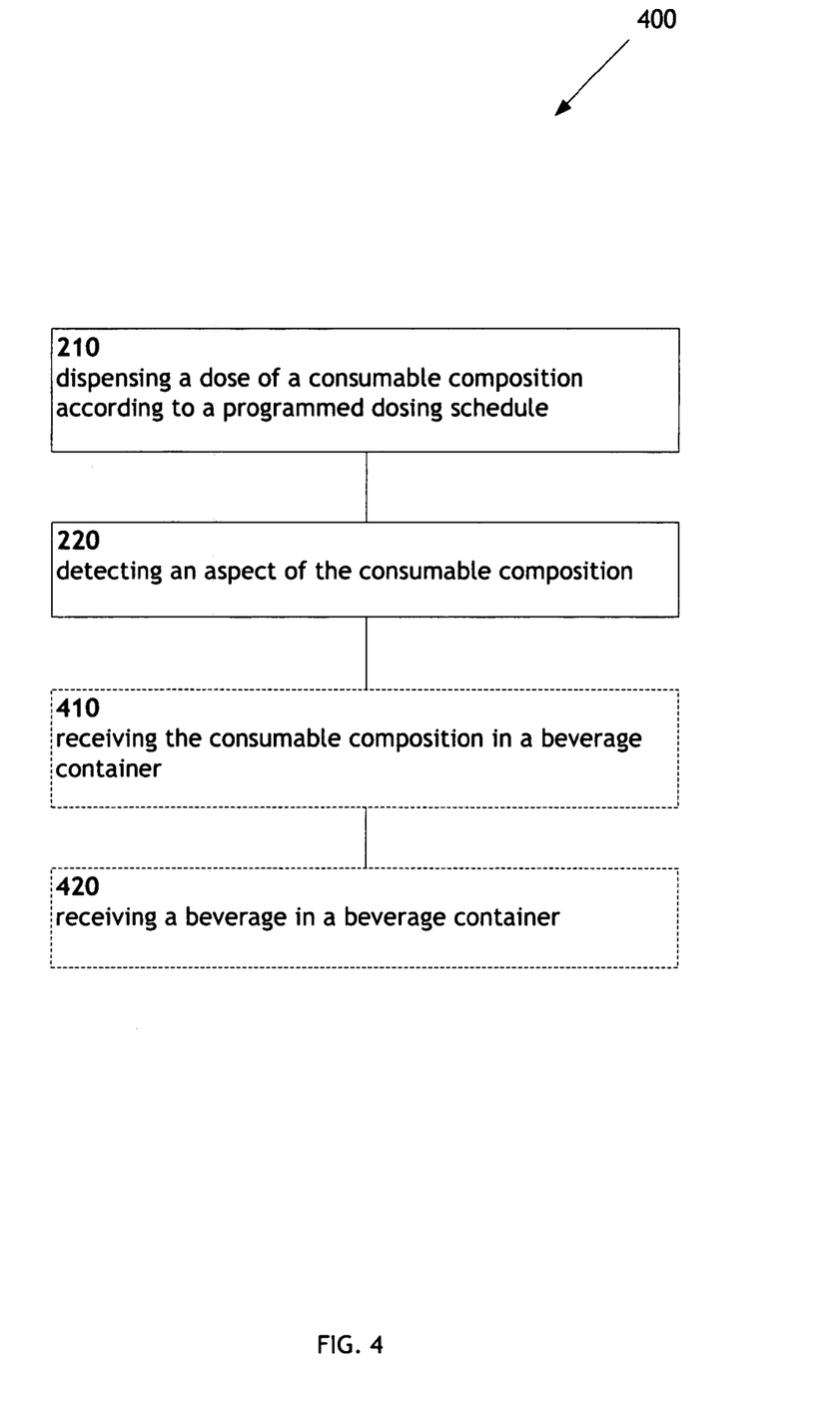
FIG. 4 is a high-level logic flowchart of a process.

FIG. 4 illustrates an operational flow 400 representing example operations related to programmed dispensing of consumable compositions. FIG. 4 illustrates an example embodiment where the example operational flow 200 of FIG. 2 may include at least one additional operation. Additional operations may include an operation 410, and/or an operation 420.

After a start operation, a dispensing operation 210, and a detecting operation 220, the operational flow 400 moves to a receiving operation 410, where the consumable composition may be received in a beverage container 110. For example, as shown in FIG. 1, the beverage container 110 may include any receptacle configured for retaining liquid or gel composition. The beverage container may include a cup, glass, mug, bowl, pitcher, jug, and the like.

Then, in a receiving operation 420, a beverage (e.g. water) may be received in the beverage container 110. For example, as shown in FIG. 1, the beverage may include any composition which may be introduced and retained in a beverage container 110, including water, soda pop, coffee, juice, milk, tea and the like.

Figure 5:
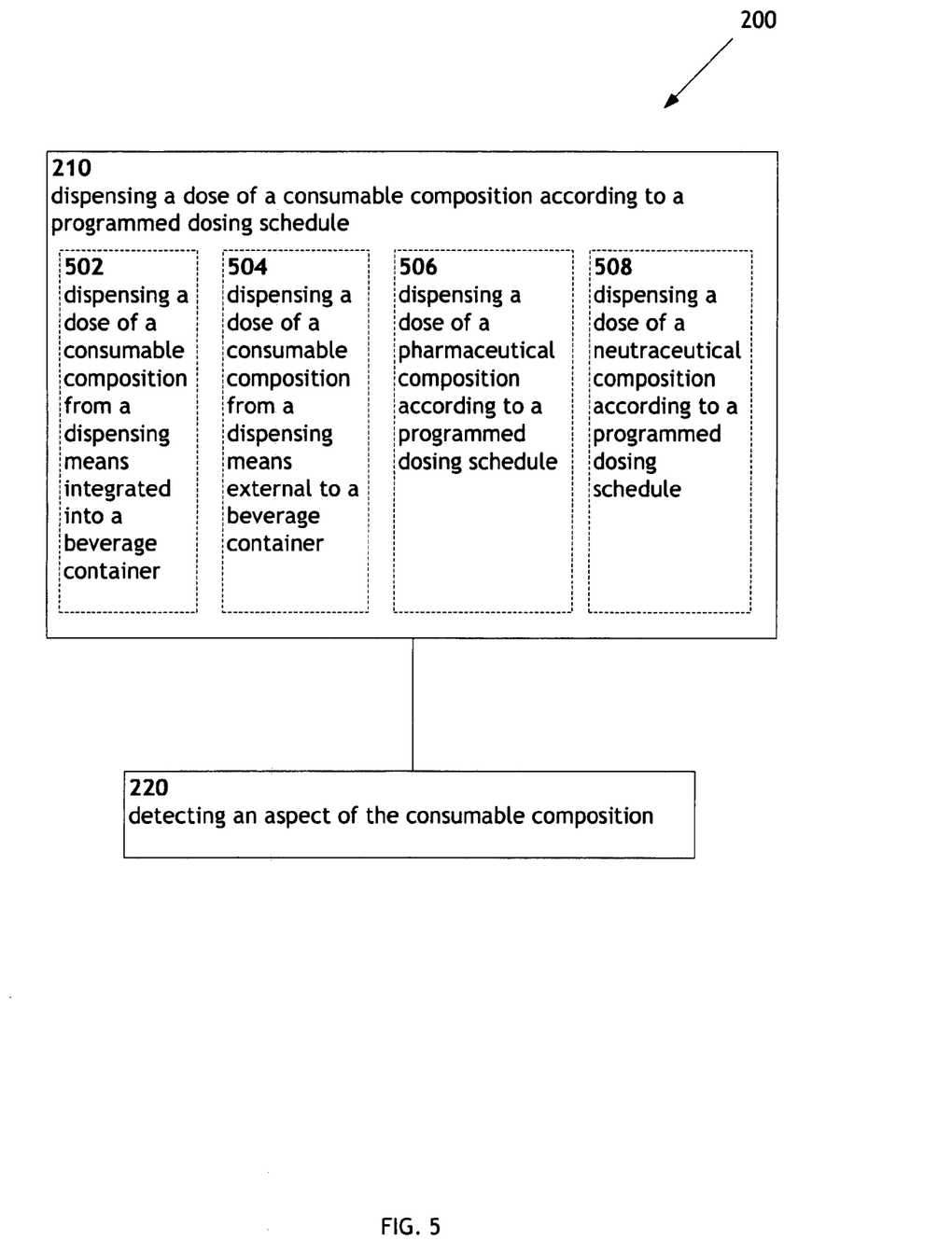
FIG. 5 is a high-level logic flowchart of a process depicting alternate implementations of FIG. 2.

FIG. 5 illustrates alternative embodiments of the example operational flow 200 of FIG. 2. FIG. 5 illustrates example embodiments where the dispensing operation 210 may include at least one additional operation. Additional operations may include an operation 502, an operation 504, an operation 506, and/or an operation 508.

At the operation 502, a dose of a consumable composition may be dispensed from a dispenser module 160 integrated (e.g. physically attached) into a beverage container. For example, as shown in FIG. 1, the integrated consumable composition dispenser module 160 may be physically incorporated as a component of the beverage container 110. The integrated consumable composition dispenser module 160 may include an acuated mechanical apparatus which opens in response to a command from dispensing logic 125, thereby dispensing a dose of the consumable composition. The beverage container 110 may be configured to receive a dose of the consumable composition via gravitational flow or by pressurized injection of the dispensed composition from the integrated consumable composition dispenser module 160.

At the operation 504, a dose of a consumable composition may be dispensed from a consumable composition dispenser module external to a beverage container 110 (e.g. a fountain-type dispenser). For example, as shown in FIG. 1, the external consumable composition dispenser module 170 may be physically separated from the beverage container 110. The external consumable composition dispenser module 170 may include a mechanical apparatus which opens in response to a command from dispensing logic 125 so as to introduce a dose of the consumable composition into the beverage container 110. The beverage container 110 may be configured to receive a dose of the consumable composition via a communicating assembly whereby the beverage container 110 may be physically coupled to the external consumable composition dispenser module 170 via a mutual conduit operably configured to allow the passage of the consumable composition between the external consumable composition dispenser module 170 and the beverage container 110.

At the operation 506, a dose of a pharmaceutical composition (e.g. an ACE inhibitor) may be dispensed according to a programmed dosing schedule. For example, the pharmaceutical composition may be any therapeutic composition to be dispensed according to a programmed dosing schedule, including, but not limited to: 5-alpha reductase inhibitor, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, antiemetics, antiepileptics, antiflatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosponates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, and the like.

At the operation 508, a dose of a neutraceutical composition (e.g. an herbal composition) may be dispensed according to a programmed dosing schedule. For example, the neutraceutical composition may be any nutritional composition to be dispensed according to a programmed dosing schedule, including, but not limited to: vitamins (e.g., ascorbic acid, pyridoxine, riboflavin), minerals (e.g., calcium salts, zinc salts, potassium salts), hormones (e.g., cortisone, pancreatin, epinephrine), biochemicals (e.g., adenosine triphosphate, coenzyme A, cysteine), glandulars (e.g., thyroid, pancreas, adrenal cortex), herbals (e.g., ginkgo, garlic, goldenseal, echinacea), and the like.

Figure 6:
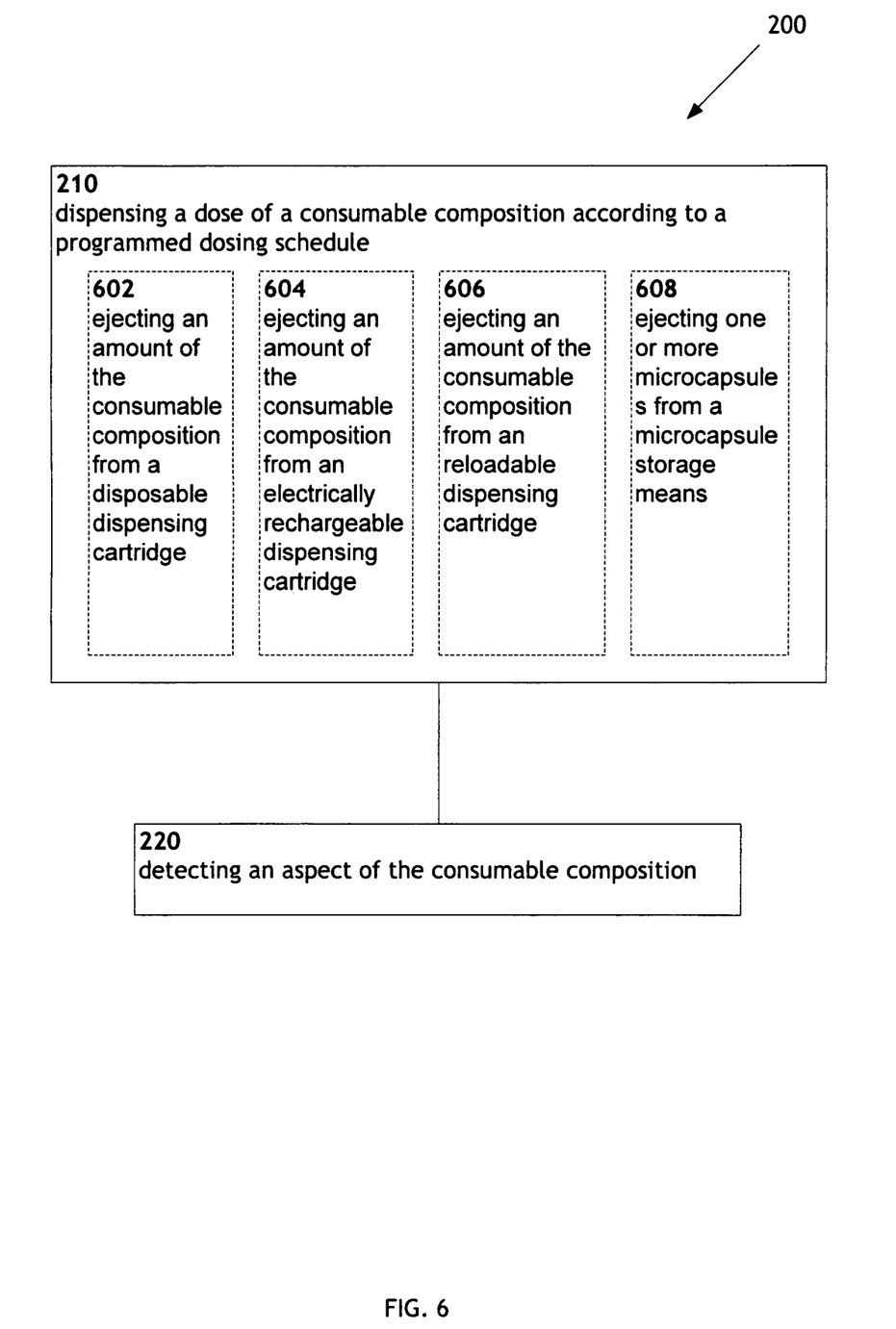
FIG. 6 is a high-level logic flowchart of a process depicting alternate implementations of FIG. 2.

FIG. 6 illustrates alternative embodiments of the example operational flow 200 of FIG. 2. FIG. 6 illustrates example embodiments where the dispensing operation 210 may include at least one additional operation. Additional operations may include an operation 602, an operation 604, an operation 606, and/or an operation 608.

At the operation 602, an amount of the consumable composition may be ejected (e.g. displaced via pressurization) from a disposable (e.g. single or limited-use) dispensing cartridge. For example, as shown in FIG. 1, the integrated consumable composition dispenser module 160, and/or the external consumable composition dispenser module 170 may be configured to receive a disposable cartridge containing the consumable composition. Upon the dispensation of some or all of the supply of the consumable composition contained in the disposable cartridge, the cartridge may be removed from the integrated consumable composition dispenser module 160, and/or the external consumable composition dispenser module 170 and a replacement cartridge containing an additional supply of the consumable composition may be inserted.

At the operation 604, an amount of the consumable composition may be ejected from an electrically rechargeable dispensing cartridge (e.g. a cartridge including a lithium ion battery). For example, the consumable composition may be ejected from the dispensing cartridge by an electrical pump integrated either into the cartridge or into the integrated consumable composition dispenser module 160, and/or external consumable composition dispenser module 170. The cartridge containing the consumable composition may include a rechargeable battery so as to provide a renewable power source for the electrical pump.

At the operation 606, an amount of the consumable composition may be ejected from a reloadable dispensing cartridge (e.g. a user 190 may add an additional amount of consumable composition to the cartridge). For example, as shown in FIG. 1, the integrated consumable composition dispenser module 160, and/or the external consumable composition dispenser module 170 may be configured to receive a reloadable cartridge containing the consumable composition. Upon the dispensation of some or all of the supply of the consumable composition contained in the disposable cartridge, the cartridge may be removed from the integrated consumable composition dispenser module 160, and/or the external consumable composition dispenser module 170, an additional amount of the consumable composition may be loaded into the cartridge, and the original cartridge replaced into the integrated consumable composition dispenser module 160, and/or the external consumable composition dispenser module 170.

At the operation 608, one or more microcapsules may be ejected from a microcapsule storage module. For example, as shown in FIG. 1, the integrated consumable composition dispenser module 160 and/or the external consumable composition dispenser module may contain one or microcapsules (e.g. enteric drug coatings). The microcapsules may contain the consumable composition. The individual microcapsules may be configured such that the release of the consumable composition therefrom varies from microcapsule to microcapsule thereby providing a controlled release of the consumable composition across a given time period.

Figure 7:
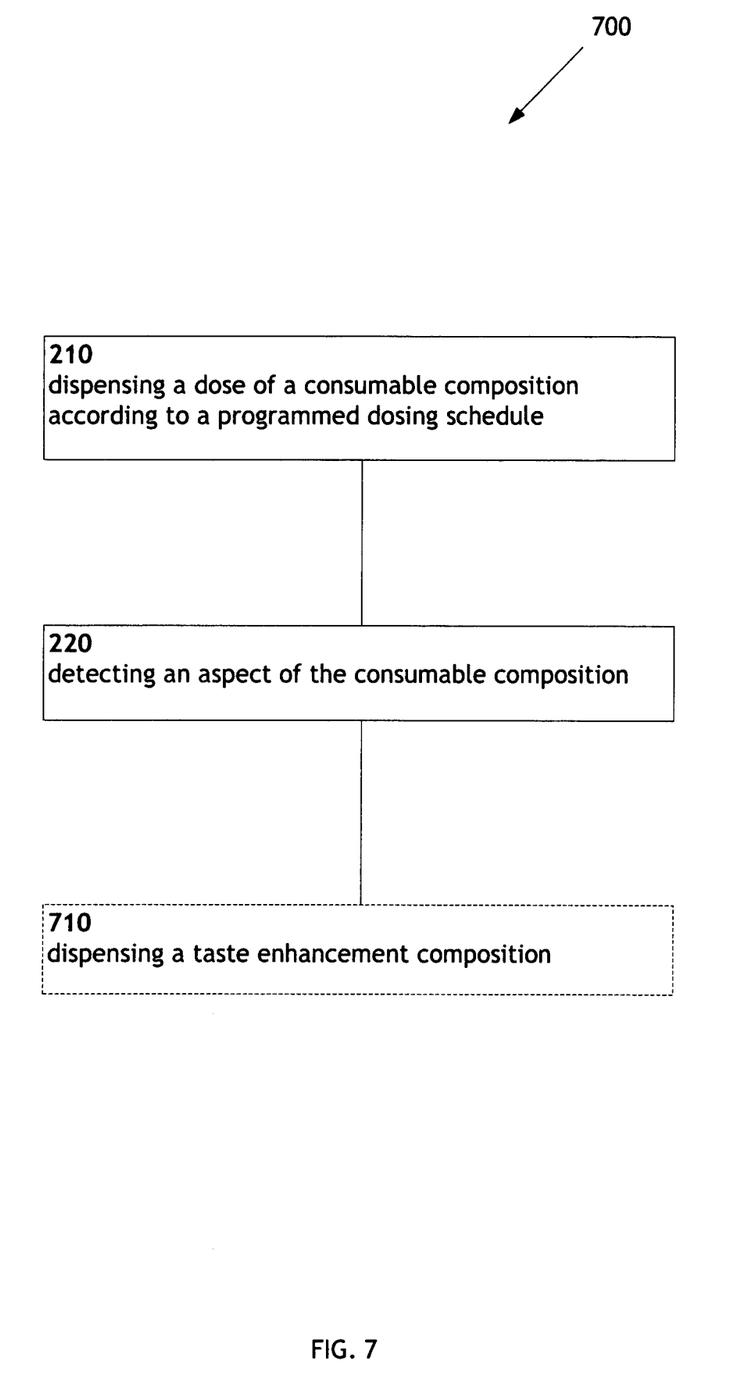
FIG. 7 is a high-level logic flowchart of a process.

FIG. 7 illustrates an operational flow 700 representing example operations related to dispensing a dose of a consumable composition. FIG. 7 illustrates an example embodiment where the example operational flow 200 of FIG. 2 may include at least one additional operation. Additional operations may include an operation 710.

After a start operation, a dispensing operation 210, and a detecting operation 220, the operational flow 700 moves to a dispensing operation 710, where a taste enhancement composition (e.g. a fruit distilate) may be dispensed. For example, as shown in FIG. 1, the dispenser module 160 may dispense a taste enhancement. The taste enhancement may include an essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or any other edible portions of a plant, meat, seafood, poultry, eggs, dairy products, fermentation product thereof, and the like.

Figure 8:
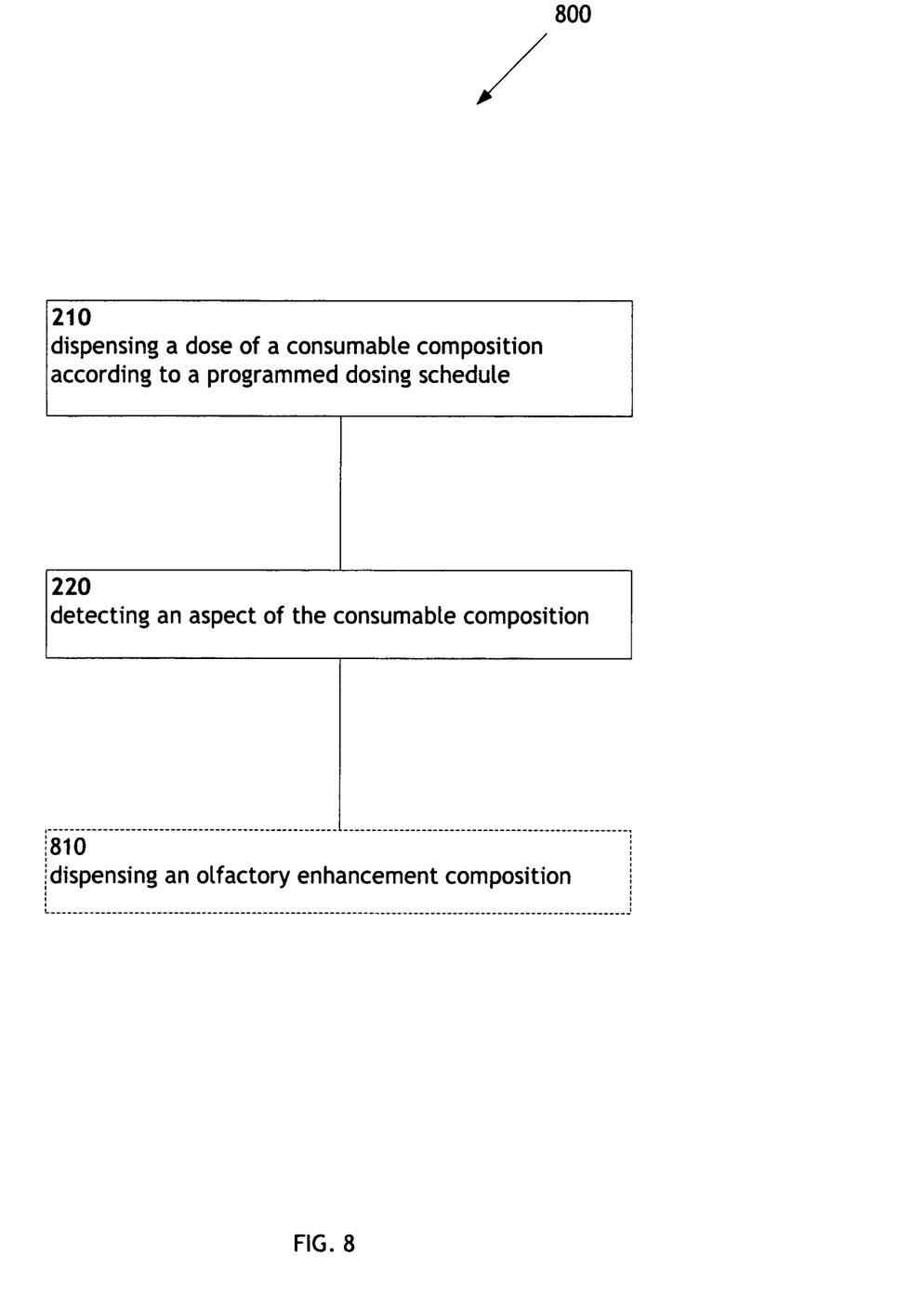
FIG. 8 is a high-level logic flowchart of a process.

FIG. 8 illustrates an operational flow 800 representing example operations related to dispensing a dose of a consumable composition. FIG. 8 illustrates an example embodiment where the example operational flow 200 of FIG. 2 may include at least one additional operation. Additional operations may include an operation 810.

After a start operation, a dispensing operation 210, and a detecting operation 220, the operational flow 800 moves to a dispensing operation 810, where an olfactory enhancement composition may be dispensed. For example, as shown in FIG. 1, the dispenser module may dispense an olfactory enhancement (e.g. ethyl proprionate). The olfactory enhancement may include diacetyl (butter), isoamyl acetate (banana), cinnamic aldehyde (cinnamon), ethyl propionate (fruit), limonene (orange) ethyl-(E,Z)-2,4-decadienoate (pear), allyl hexanoate (pineapple), ethyl maltol (sugar, cotton candy), methyl salicylate (wintergreen), benzaldehyde (bitter almond), and the like.

Figure 9:
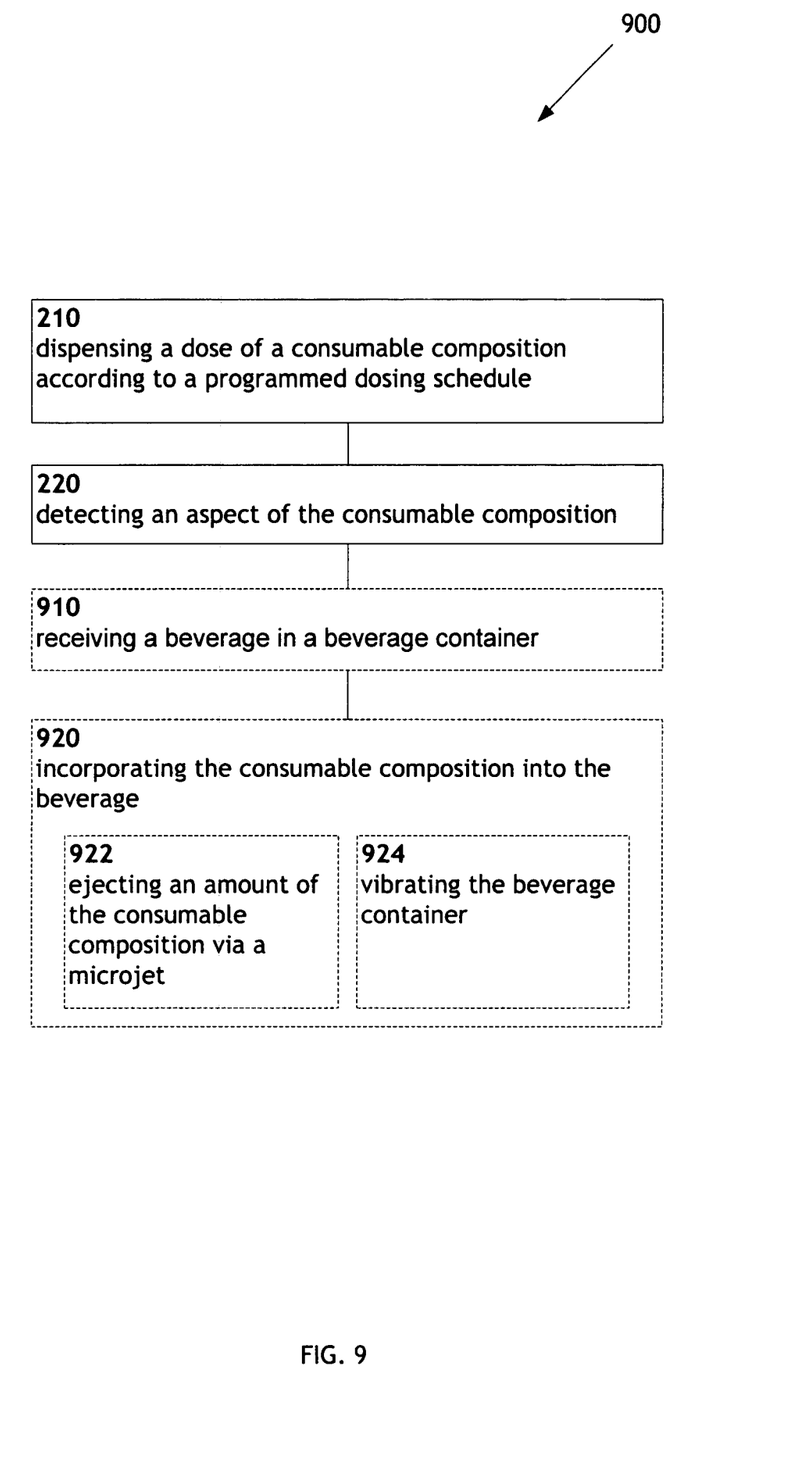
FIG. 9 is a high-level logic flowchart of a process.

FIG. 9 illustrates an operational flow 900 representing example operations related to incorporating a programmed dose of a consumable composition into a beverage. FIG. 9 illustrates an example embodiment where the example operational flow 200 of FIG. 2 may include at least one additional operation. Additional operations may include an operation 910, an operation 920, an operation 922, and/or an operation 924.

After a start operation, a dispensing operation 210, and a detecting operation 220, the operational flow 900 moves to a receiving operation 910, where a beverage may be received in a beverage container. For example, as shown in FIG. 1, the beverage container 110 may include any receptacle configured for retaining liquid or gel composition. The beverage container may include a cup, glass, mug, bowl, pitcher, jug, and the like. The beverage may include any composition which may be introduced and retained in a beverage container, including water, soda pop, coffee, juice, milk, tea and the like.

Then, in an incorporation operation 920, the consumable composition may be incorporated (e.g. physically distributed) into the beverage. For example, as shown in FIG. 1, the integrated consumable composition dispenser module 160, and/or the external consumable composition dispenser module 170 may dispense the consumable composition such that it becomes mixed with or may dissolve in the beverage.

At the operation 922, an amount of the consumable composition may be ejected into the beverage container via a microjet (e.g. device having a small outlet orifice whereby a fluid may be dispensed at high velocity). For example, as shown in FIG. 1, the integrated consumable composition dispenser module 160, and/or the external consumable composition dispenser module 170 may comprise a microjet operably configured to dispense the consumable composition into the beverage such that the motion of the consumable composition may induce turbulence in the beverage contained in the beverage container, thereby mixing and/or dissolving the consumable composition in the beverage.

At the operation 924, the beverage container may be vibrated. For example, as shown in FIG. 1, the beverage container 110 may include an asymmetrical rotating mass operably coupled to a motor. Upon application of power to the motor, the mass may be rotated such that it induces vibration in the beverage container 110. Such vibration may induce turbulence in the beverage contained in the beverage container 110, thereby mixing and/or dissolving the consumable composition in the beverage.

Figure 10:
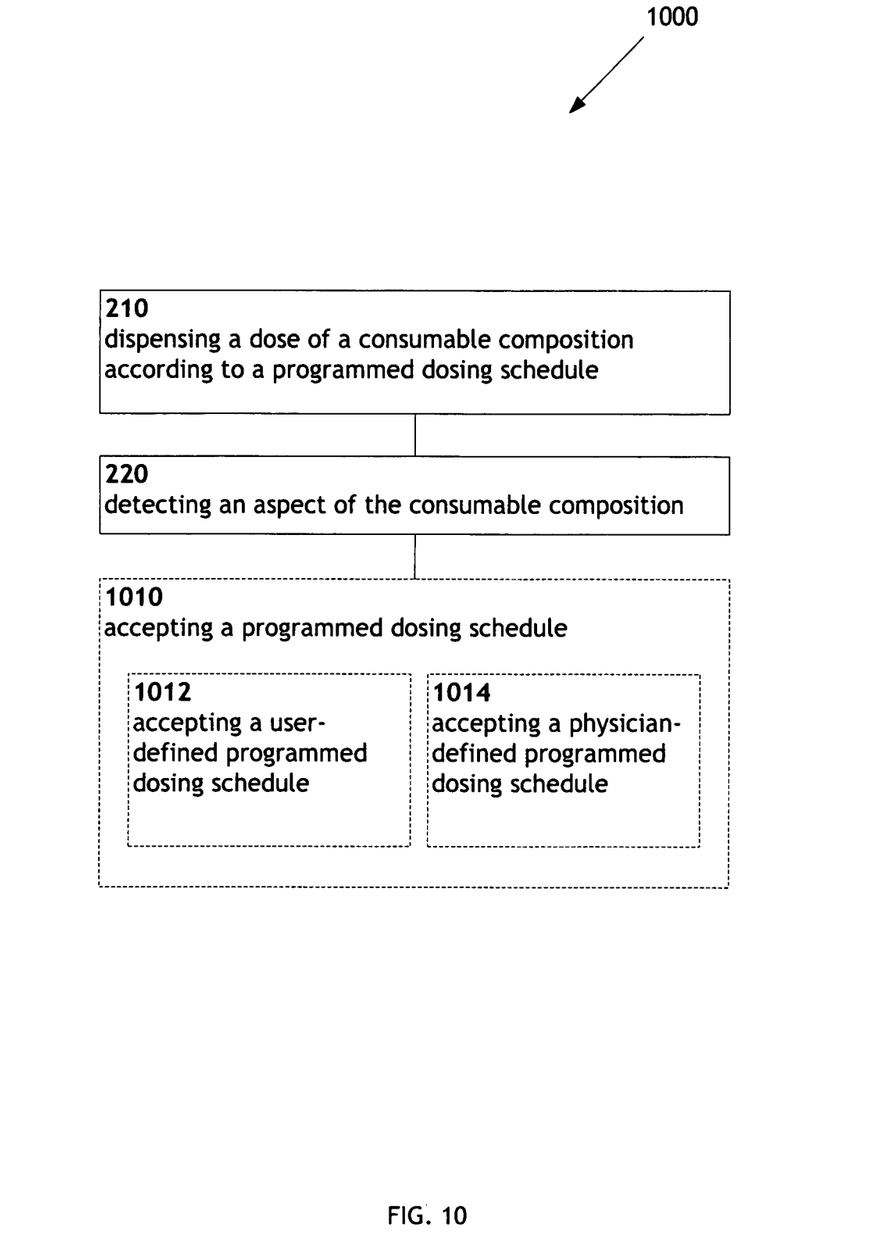
FIG. 10 is a high-level logic flowchart of a process.

FIG. 10 illustrates an operational flow 1000 representing example operations related to programmed dispensing of consumable compositions. FIG. 10 illustrates an example embodiment where the example operational flow 200 of FIG. 2 may include at least one additional operation. Additional operations may include an operation 1010, an operation 1012, and/or an operation 1014.

After a start operation, a dispensing operation 210, and a detecting operation 220, the operational flow 1000 moves to an accepting operation 1010, where a programmed dosing schedule may be accepted (e.g. data representing a physician-prescribed medication regimine stored in an electronic medium may be processed). For example, as shown in FIG. 1, the dispensing logic 125 may accept data representing a programmed dosing schedule and may control dispensing of the consumable composition by the integrated consumable composition dispenser module 160, and/or the external consumable composition dispenser module 170 according to the programmed dosing schedule.

At the operation 1012, a user-defined (e.g. a user entering dosing related data via a key-pad or touchscreen) programmed dosing schedule may be accepted. For example, as shown in FIG. 1, a user 190 may provide a user-defined programmed dosing schedule via a manual input module 146 of user interface 140. The user-defined programmed dosing schedule may be maintained in memory 126. Dispensing logic 125 may accept a user-defined programmed dosing schedule from the memory 126 and may control dispensing of the consumable composition by the integrated consumable composition dispenser module 160, and/or the external consumable composition dispenser module 170 according to the user-defined programmed dosing schedule.

At the operation 1014, a physician-defined programmed dosing schedule (e.g. a physician entering dosing data into a remote electronic database) may be accepted. For example, as shown in FIG. 1, a physician may access a monitoring system 180 and may provide a physician-defined programmed dosing schedule. The monitoring system 180 may transmit the physician-defined programmed dosing schedule to the system 100 via a communications module 130. The physician-defined programmed dosing schedule may be maintained in memory 126. Dispensing logic 125 may accept a physician-defined programmed dosing schedule from the memory 126 and may control dispensing of the consumable composition by the integrated consumable composition dispenser module 160, and/or the external consumable composition dispenser module 170 according to the physician-defined programmed dosing schedule.

Monitoring system 180 may also transmit a notification (e.g. a notification that a programmed dosing schedule has been transmitted to the system 100) to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing system 184 (e.g. a personal digital assistant (PDA), personal computer, laptop, music player and/or gaming device).

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art Will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A method for administering a consumable composition, the method comprising:
   obtaining dosing schedule data associated with a consumable composition consumption regimen for at least one user;
   releasing at least one dose of a consumable composition from a consumable composition storage into a container according to the dosing schedule data;
   sensing at least one aspect of at least one dose of the consumable composition that has been dispensed into the container;
   transmitting data associated with a sensed aspect of the at least one dose of the consumable composition that has been dispensed into the container; and
   verifying compliance by the user with the consumable composition consumption regimen from the data associated with the sensed aspect of the at least one dose of the consumable composition that has been dispensed into the container.

2. A system for administering a consumable composition, the system comprising:
   a computing device configured for obtaining dosing schedule data associated with a consumable composition consumption regimen for at least one user;

a dispenser device configured for releasing at least one dose of a consumable composition from a consumable composition storage into a container according to the dosing schedule data; and at least one sensor configured for sensing at least one aspect of at least one dose of the consumable composition that has been dispensed into the container;

at least one transceiver configured for transmitting data associated with a sensed aspect of the at least one dose of the consumable composition that has been dispensed into the container; and a verification module configured for verifying compliance by the user with the consumable composition consumption regimen from the data associated with the sensed aspect of the at least one dose of the consumable composition that has been dispensed into the container.

3. The system of claim 2, further comprising:

at least one container configured for receiving the consumable composition, wherein the at least one container includes the at least one sensor.

4. The system of claim 2, wherein the dispenser device configured for releasing at least one dose of a consumable composition from a consumable composition storage into a container according to the dosing schedule data includes:

a dispenser device coupled to a container receiving the dose of a consumable composition.

5. The system of claim 2, wherein the dispenser device configured for releasing at least one dose of a consumable composition from a consumable composition storage into a container according to the dosing schedule data includes:

a dispenser device that is not coupled to a container receiving the dose of a consumable composition.

6. The system of claim 2, wherein the dispenser device configured for releasing at least one dose of a consumable composition from a consumable composition storage into a container according to the dosing schedule data includes:

a dispenser device configured for dispensing a dose of a pharmaceutical composition according to a programmed dosing schedule.

7. The system of claim 2, wherein the dispenser device configured for releasing at least one dose of a consumable composition from a consumable composition storage into a container according to the dosing schedule data includes:

a dispenser device configured for dispensing a dose of a neutraceutical composition according to a programmed dosing schedule.

8. The system of claim 2, wherein the dispenser device configured for releasing at least one dose of a consumable composition from a consumable composition storage into a container according to the dosing schedule data includes:

a dispenser device configured for ejecting an amount of the consumable composition from a disposable dispensing cartridge.

9. The system of claim 2, wherein the dispenser device configured for releasing at least one dose of a consumable composition from a consumable composition storage into a container according to the dosing schedule data includes:

a dispenser device configured for ejecting an amount of the consumable composition from an electrically rechargeable dispensing cartridge.

10. The system of claim 2, wherein the dispenser device configured for controlling dispensing releasing at least one dose of a consumable composition from a consumable composition storage into a container according to the dosing schedule data includes:

a dispenser device configured for ejecting an amount of the consumable composition from a reloadable dispensing cartridge.

11. The system of claim 2, wherein the dispenser device configured for releasing at least one dose of a consumable composition from a consumable composition storage into a container according to the dosing schedule data includes:

a dispenser device configured for ejecting one or more microcapsules from a microcapsule storage module.

12. The system of claim 2, wherein the dispenser device configured for releasing at least one dose of a consumable composition from a consumable composition storage into a container according to the dosing schedule data is further configured for:

dispensing a second consumable composition including a taste enhancement composition.

13. The system of claim 2, wherein the dispenser device configured for releasing at least one dose of a consumable composition from a consumable composition storage into a container according to the dosing schedule data is further configured for:

dispensing a second consumable composition including an olfactory enhancement composition.

14. The system of claim 2, further comprising:

a container configured for receiving a beverage; and a mixing apparatus configured for incorporating a dispensed consumable composition into the beverage.

15. The system of claim 14, wherein the mixing apparatus configured for incorporating a dispensed consumable composition into the beverage further comprises:

at least one microjet configured for ejecting an amount of the consumable composition.

16. The system of claim 14, wherein the mixing apparatus configured for incorporating a dispensed consumable composition into the beverage further comprises:

a rotating mass configured for vibrating the container.

17. The system of claim 2, further comprising:

a computing device configured for accepting a programmed dosing schedule.

18. The system of claim 17, wherein the computing device configured for accepting a programmed dosing schedule further comprises:

a computing device configured for accepting a user-defined programmed dosing schedule.

19. The system of claim 17, wherein the computing device configured for accepting a programmed dosing schedule further comprises:

a computing device configured for accepting a physician-defined programmed dosing schedule.

20. A system for administering a consumable composition, the system comprising:

circuitry for obtaining dosing schedule data associated with a consumable composition consumption regimen for at least one user;

circuitry for releasing at least one dose of a consumable composition from a consumable composition storage into a container according to the dosing schedule data;

circuitry for sensing at least one aspect of at least one dose of the consumable composition that has been dispensed into the container;

circuitry for transmitting data associated with a sensed aspect of the at least one dose of the consumable composition that has been dispensed into the container; and circuitry for verifying compliance by the user with the consumable composition consumption regimen from the data associated with the sensed aspect of the at least one dose of the consumable composition that has been dispensed into the container.

21. The system of claim 2, wherein the at least one sensor configured for sensing at least one aspect of the at least one dose of the consumable composition includes:
   at least one of an electromagnetic sensor, a position sensor, an emission sensor, a spectrophotometer sensor, an infrared sensor, or a biometric sensor.

22. The system of claim 2, wherein the at least one sensor configured for sensing at least one aspect of the at least one dose of the consumable composition includes:
   at least one sensor configured for detecting at least one of: an amount of consumable composition dispensed into a container, an amount of consumable composition present in a container, an amount of the composition removed from a container, an identity of the consumable composition, or an identity of a user.

* * * * *

UNITED STATES PATENT AND TRADEMARK OFFICE
CERTIFICATE OF CORRECTION

PATENT NO.        : 8,788,380 B2                                    Page 1 of 1
APPLICATION NO.   : 11/998461
DATED             : July 22, 2014
INVENTOR(S)       : Hyde et al.

It is certified that error appears in the above-identified patent and that said Letters Patent is hereby corrected as shown below:

Title Page, item (75) Inventors delete "Eric D. Leuthardt" and replace with --Eric C. Leuthardt--

Title Page, item (75) Inventors delete "Lovell L. Wood, Jr." and replace with --Lowell L. Wood, Jr.--

In the Claims

Column 11, Line 64, Claim 10 delete "configured for controlling dispensing releasing at least one" and replace with --configured for releasing at least one--

Signed and Sealed this
Thirtieth Day of December, 2014

Michelle K. Lee
*Deputy Director of the United States Patent and Trademark Office*